(12) United States Patent
Poutiatine et al.

(10) Patent No.: US 10,149,645 B2
(45) Date of Patent: Dec. 11, 2018

(54) SYSTEM FOR TRACKING AND RESPONDING TO SOLAR RADIATION EXPOSURE FOR IMPROVEMENT OF ATHLETIC PERFORMANCE

(71) Applicant: Andrew Poutiatine, Mill Valley, CA (US)

(72) Inventors: Andrew Poutiatine, Mill Valley, CA (US); Alison Park, Mill Valley, CA (US)

(*) Notice: Subject to any disclaimer, the term of this patent is extended or adjusted under 35 U.S.C. 154(b) by 0 days.

(21) Appl. No.: 15/926,282

(22) Filed: Mar. 20, 2018

(65) Prior Publication Data

US 2018/0249944 A1 Sep. 6, 2018

Related U.S. Application Data

(63) Continuation-in-part of application No. 15/648,158, filed on Jul. 12, 2017.

(60) Provisional application No. 62/473,937, filed on Mar. 20, 2017, provisional application No. 62/473,940, filed on Mar. 20, 2017, provisional application No. 62/361,414, filed on Jul. 12, 2016, provisional application No. 62/380,455, filed on Aug. 28, 2016, provisional application No. 62/404,131, filed on Oct. 4, 2016, provisional application No. 62/434,184, filed (Continued)

(51) Int. Cl.
*A01K 43/00* (2006.01)
*A61B 5/00* (2006.01)
*G01J 1/42* (2006.01)
*A63B 24/00* (2006.01)

(52) U.S. Cl.
CPC .............. *A61B 5/441* (2013.01); *A61B 5/486* (2013.01); *A61B 5/6804* (2013.01); *A61B 5/7278* (2013.01); *A63B 24/0075* (2013.01); *G01J 1/429* (2013.01); *G01J 1/4209* (2013.01); *A61B 2503/10* (2013.01); *A61B 2560/0242* (2013.01); *G01J 2001/4266* (2013.01)

(58) Field of Classification Search
CPC ....... A61B 5/441; A61B 5/486; A61B 5/6804; A61B 5/7278; A61B 2503/10; A61B 2560/0242; A63B 24/0075; G01J 1/02; G01J 1/42; G01J 1/50; G01J 1/0233; G01J 1/0219; G01J 1/0238; G01J 1/0266; G01J 1/0271; G01J 1/4228; G01J 1/4209; G01J 1/029; G01J 1/429; G01J 2001/4266

See application file for complete search history.

(56) References Cited

U.S. PATENT DOCUMENTS

2017/0191866 A1* 7/2017 Balooch .................. G01J 1/429

* cited by examiner

*Primary Examiner* — Jamil Ahmed
(74) *Attorney, Agent, or Firm* — Run8 Patent Group, LLC; Peter Miller

(57) ABSTRACT

One variation of a system for tracking and responding to Sun exposure includes: a housing configured to transiently attach to a port on a first garment; a jack coupled to the housing configured to transiently engage a port on the first garment; a radiation sensor arranged in the housing and configured to detect solar radiation incident on the housing; and a controller configured to: read an identifier of the first garment from the port via the jack; based on the identifier, estimate a skin exposure of a user wearing the first garment; read an solar radiation value from the radiation sensor at a first time;

(Continued)

and, based on the solar radiation value and the skin exposure, estimate an solar radiation exposure of the user at the first time.

20 Claims, 6 Drawing Sheets

Related U.S. Application Data on Dec. 14, 2016, provisional application No. 62/525,872, filed on Jun. 28, 2017.

SYSTEM FOR TRACKING AND RESPONDING TO SOLAR RADIATION EXPOSURE FOR IMPROVEMENT OF ATHLETIC PERFORMANCE

CROSS-REFERENCE TO RELATED APPLICATIONS

This Application claims the benefit of U.S. Provisional Application No. 62/473,937, filed on 20 Mar. 2017, and U.S. Provisional Application No. 62/473,940, filed on 20 Mar. 2017, both of which are incorporated in their entireties by this reference.

This Application is also a continuation-in-part application of U.S. patent application Ser. No. 15/648,158, filed on 12 Jul. 2017, which claims the benefit of U.S. Provisional Application No. 62/361,414, filed on 12 Jul. 2016, U.S. Provisional Application No. 62/380,455, filed on 28 Aug. 2016, U.S. Provisional Application No. 62/404,131, filed on 4 Oct. 2016, and U.S. Provisional Application No. 62/434,184, filed on 14 Dec. 2016, all of which are incorporated in their entireties by this reference.

TECHNICAL FIELD

This invention relates generally to the field of sports medicine and more specifically to a new and useful system for tracking and responding to solar radiation exposure for improvement of athletic performance in the field of sports medicine.

DESCRIPTION OF THE EMBODIMENTS

The following description of embodiments of the invention is not intended to limit the invention to these embodiments but rather to enable a person skilled in the art to make and use this invention. Variations, configurations, implementations, example implementations, and examples described herein are optional and are not exclusive to the variations, configurations, implementations, example implementations, and examples they describe. The invention described herein can include any and all permutations of these variations, configurations, implementations, example implementations, and examples.

1. System

Figure 1:
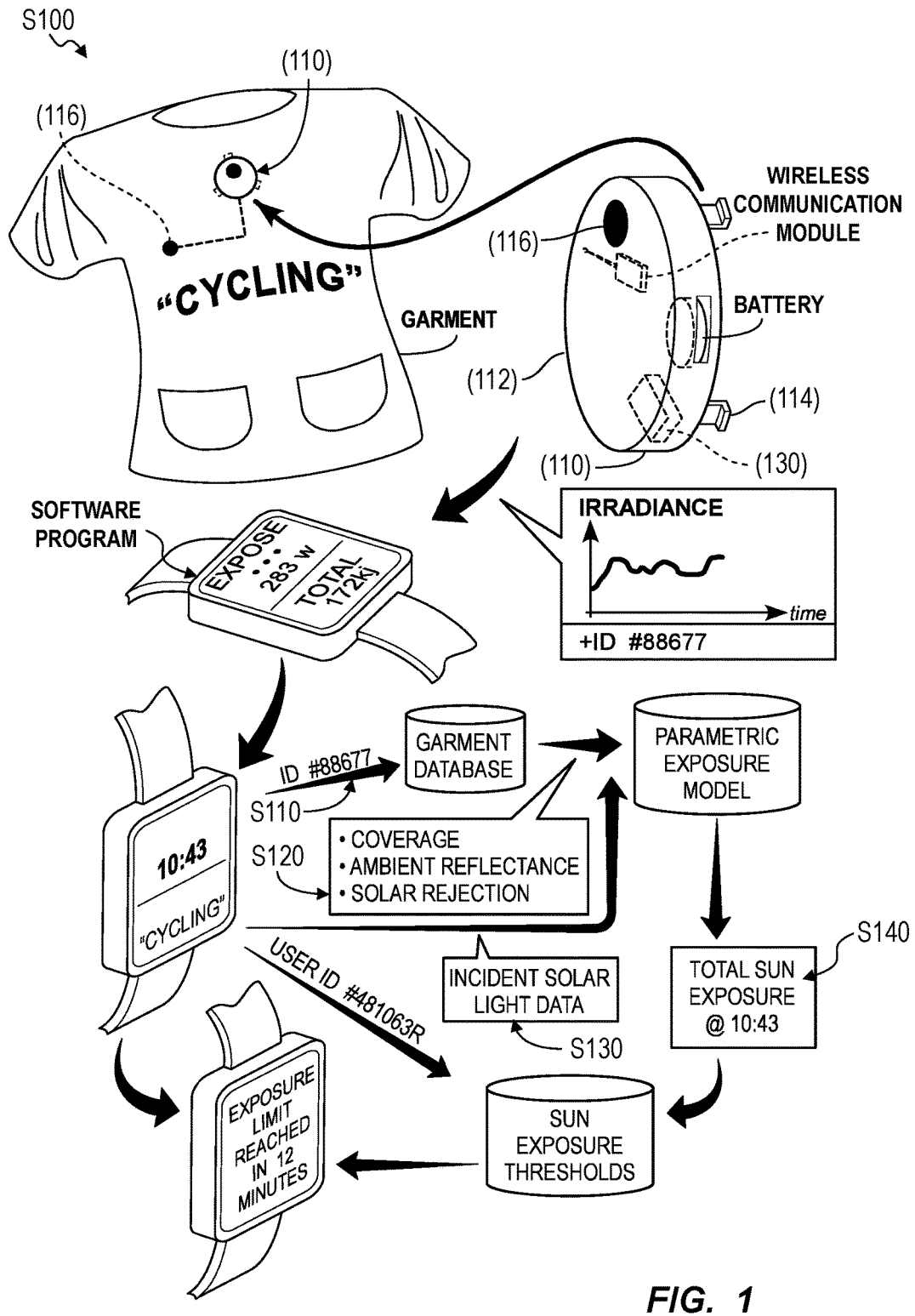
FIG. 1 is a flowchart representation of a system.
Figure 2:
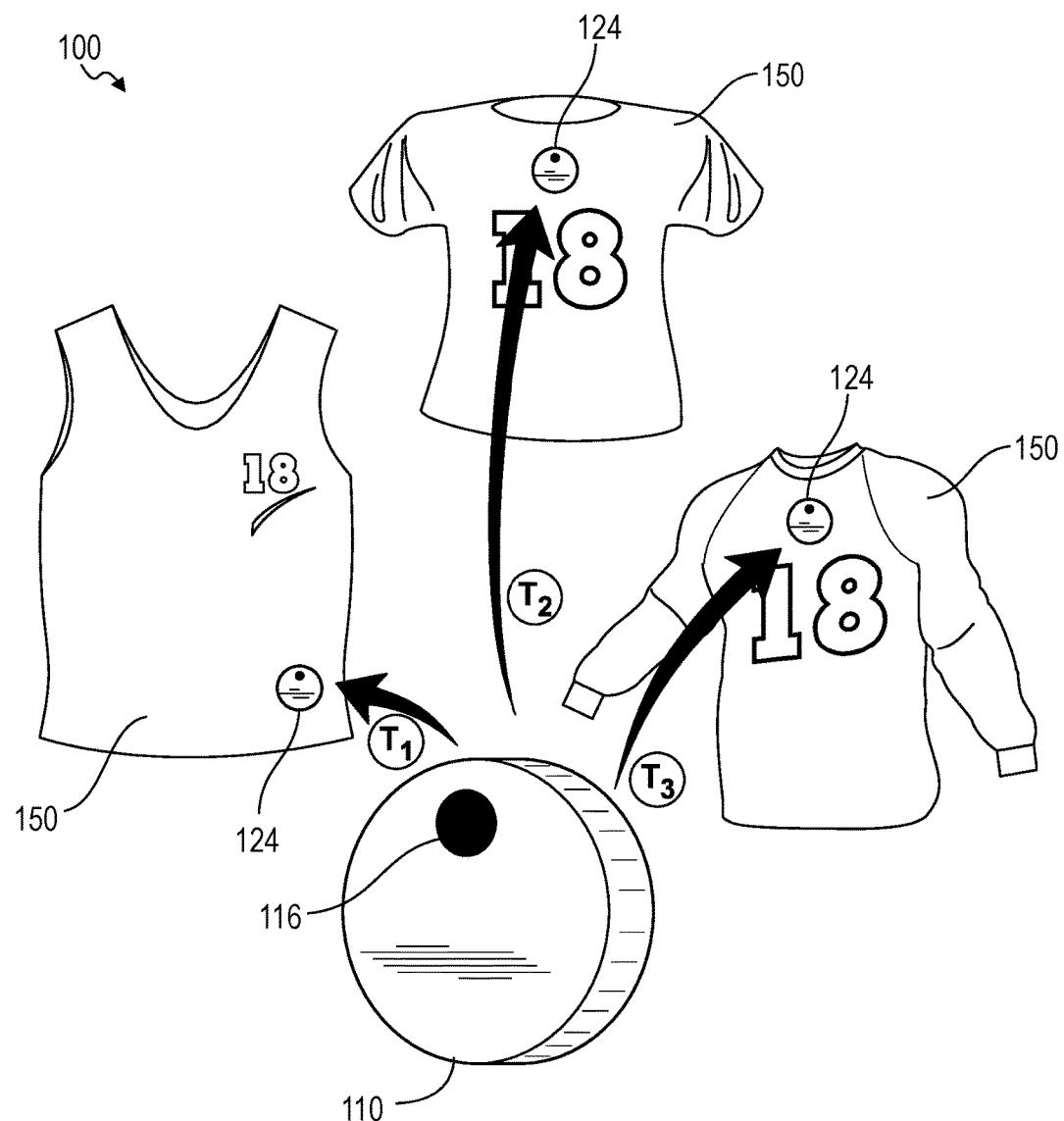
FIG. 2 is a schematic representation of one variation of the system.

As shown in FIGS. 1 and 2, a system 100 for tracking and responding to Sun exposure for improvement of athletic performance includes: a housing 112 configured to transiently attach to a port 124 on a garment 150; a jack 114 coupled to the housing 112 configured to transiently engage a port 124 on the garment 150; a radiation sensor 116 arranged in the housing 112 and configured to detect one or more wavelength bands of solar radiation incident on the housing 112; and a controller 130 configured to: read an identifier of the garment 150 from the port 124 via the jack 114; based on the identifier, estimate a skin exposure of a user wearing the garment 150; read a solar radiation value from the radiation sensor 116 at a first time; and, based on the solar radiation value and the skin exposure, estimate a solar radiation exposure (defined herein as ultraviolet, visible and/or infrared electromagnetic radiation exposure) of the user at the first time.

In one variation of the system, the controller 130 can also be configured to serve a prompt to the user to reduce solar radiation exposure in response to an estimated level of solar radiation exposure on the user's skin exceeding a threshold value.

1.1 Applications

The system 100 includes a garment 150 and an exposure-tracking module 110 that cooperate to form a "smart garment" configured to track solar radiation exposure at one known location on the garment 150. The system 100 also includes an identification module integrated into the garment 150 and configured to communicate various data to the exposure-tracking module 110 when the exposure-tracking module no is connected to a port 124 on the garment 150. A software program—such as executing at a remote server or locally by the controller 130 of the exposure-tracking module 110—can then access skin coverage afforded by the garment 150, solar radiation deflection properties of the garment's material, ambient reflectance of a ground surface common to a type of outdoor activity associated with the garment 150, a location of the port 124 on the garment 150, use and exposure history, and/or various other garment-related data. The software program can then merge these garment-related data with solar radiation (e.g., UV-A, UV-B, UV-C, visible light, and/or infrared light) exposure detected by the exposure-tracking module 110 at one instant in time to estimate a solar radiation exposure on a user's skin at a specific instant in time. By integrating this total solar radiation exposure over a duration of a training session (or a competition), the computer system 100 can track the user's total solar radiation exposure throughout this period of time and provide guidance to the user for managing her Sun exposure, such as by serving a prompt to the user's smartphone or smartwatch to apply Sunscreen, seek shade, postpone outdoor activity, and/or add layers of clothing and protective gear (such as sunglasses, hats, etc.) to cover more skin.

Figure 5A:
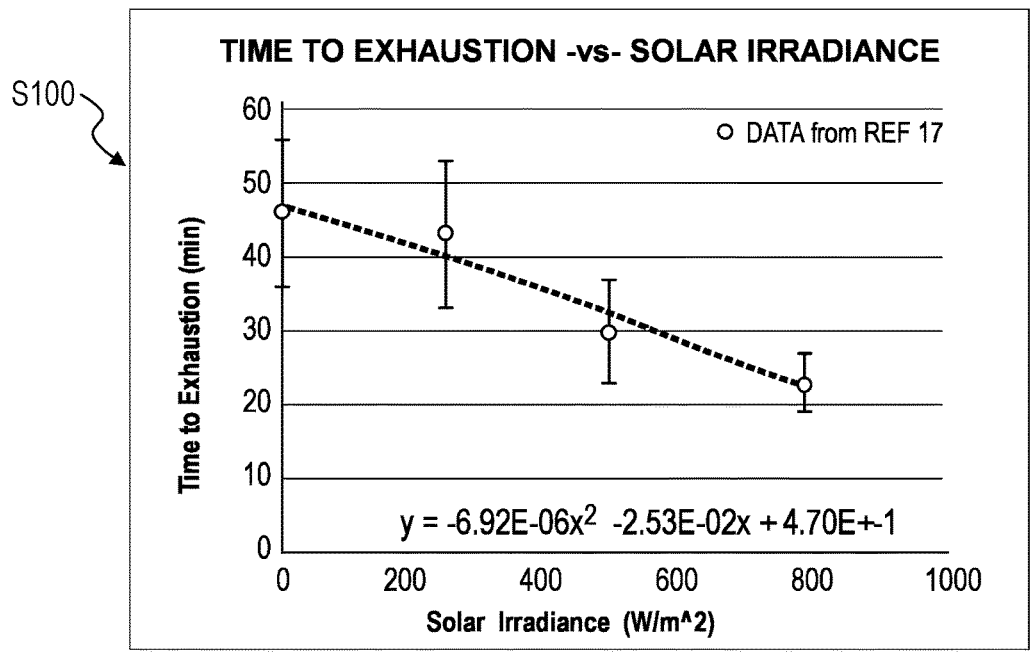
FIGS. 5A and 5B are graphical representations of variations of the system.
Figure 5B:
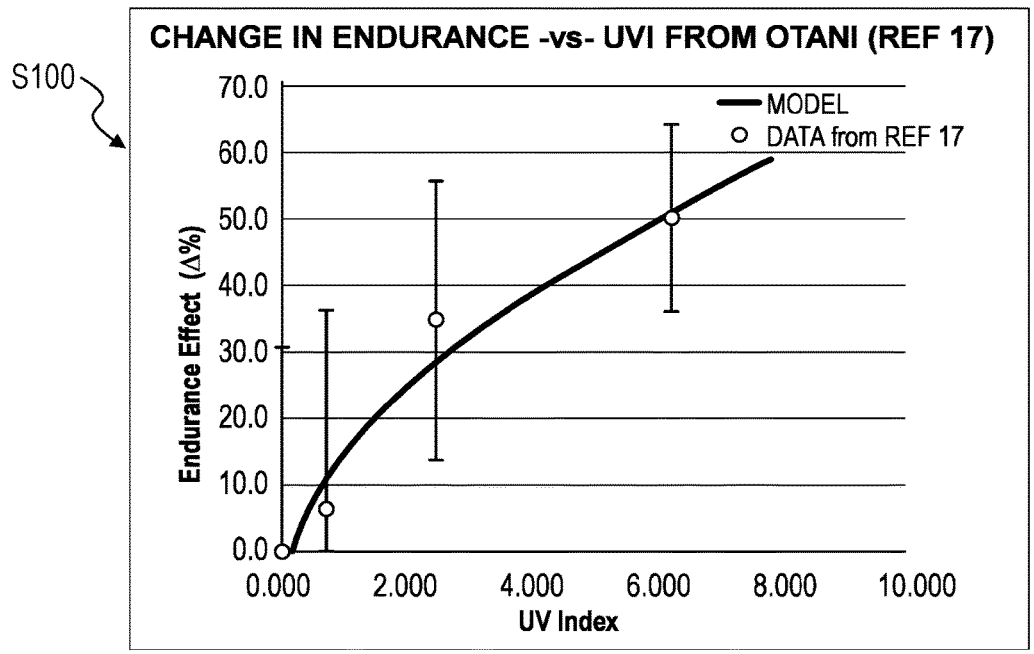

Generally, human performance in sport and athletics may be impacted by solar radiation exposure, as shown in FIGS. 5A and 5B. For example, excess sun exposure may increase an athlete's skin temperature and/or trigger other processes in the athlete's body that reduce the athlete's short-term (e.g., immediate) time to exhaustion, power output, and overall performance during a current training session or competition. Excess Sun exposure may also extend the athlete's recovery time after exertion, yielding reduced performance during a next practice session or upcoming competition. Excess Sun exposure may also yield heat rash and Sunburn that negatively affect the athlete's future mobility and adversely affect the athlete's immediate performance and long-term health through other mechanisms. In particular, when regularly engaging in an outdoor sport—such as running, cycling, football, baseball, soccer, field hockey, lacrosse, cross country skiing, canoeing, kayaking, swimming, golf, and tennis—an athlete may be exposed to sufficient Sunlight to maintain healthy levels of vitamin D, which may yield higher bone density, improved athletic performance, reduced injury risk, and improved muscle recovery in the mid- to long-terms. However, over-exposure to Sunlight may yield immediate decreases in the athlete's performance (e.g., during practice and during competition), such as in the form of reduced power output and reduced endurance.

The system 100 can therefore include: a smart garment 150 configured to monitor incident solar radiation at one point or one limited area over a user during a training or competition session. The system 100 can transform incident solar radiation (e.g., UV light, visible light, and/or infrared light) data and known parameters of the smart garment 150 into a measurement of total exposure across the user's body. Based on this measurement of total solar radiation exposure for the user, including direct, diffuse and reflected radiation exposure, the configuration and material of the garment 150, reflectivity of ambient surfaces common to an associated sport (e.g., grass for soccer, turf for football, asphalt for cycling, snow for skiing, etc.), and the location of the exposure-tracking module 110 on the garment 150, the system 100 can provide real-time, predictive guidance to the user (or to the user's coach, parent, etc.) for managing subsequent sun exposure during the session to improve or maintain the user's performance.

The system 100 is described below as including: a garment 150, such as a shirt or jersey, worn by a user; an exposure-tracking module 110 transiently installed on the garment 150, collecting garment 150 identification and solar radiation exposure data, and wirelessly transmitting these data to a local smartphone, smartwatch, or other mobile computing device nearby. The system 100 can cooperate with a remote name mapping system ("NMS") to link the garment's identifier to garment-related data. The system 100 can also execute a software package, which a mobile computing device of the user can execute. The software package can be configured to: retrieve garment-related-data from the NMS; process garment 150 identification and solar radiation exposure data locally and substantially in real-time; and selectively return notifications to the user or to the user's coach. However, the exposure-tracking module 110 can alternatively transmit the foregoing data to a remote server, such as via a local mobile computing device or hub; and the software package can execute on the remote server. Yet alternatively, the identification module integrated into the garment 150 can store various garment-related data, such as garment 150 configuration, solar rejection properties (i.e. absorption and/or reflection of one or more bands or solar radiation), reflectivity of ambient surfaces common to an activity associated with the garment 150, etc., and can return these data to the exposure-tracking module 110 when connected to the garment 150 before or during a session; and the exposure-tracking module 110 can execute the software program locally to track the user's ultraviolet exposure during the session and to automatically communicate prompts to a local mobile computing device affiliated with the user (or the user's coach, parent, etc.). However, elements of the system 100 can be of any other form and packaged in any other way to collect and process solar radiation data during a user's training session.

1.2 Garment

The system 100 includes a garment 150 configured to be worn by a user. For example, the garment 150 can include: short-sleeved, long-sleeved, or sleeveless soccer, baseball, football, running, cycling, golf, lacrosse, or tennis jersey; a skiing coat; athletic shorts; a football or cycling helmet; a baseball cap; a swimming suit; or any other soft or hard garment 150 configured to cover a region of a user's body when worn.

In one variation, elements of the system 100 are integrated into a ski pole, a ski, a bicycle frame or component, a backpack, a hydration pack, a shoe, a flotation vest, a helmet, a hat, a wrist band, or other sport- or activity-related object; and the software program implements methods and techniques to identify the object, track ultraviolet exposure via sensors in the exposure-tracking module 110 connected to the object, and to serve Sun exposure-related guidance to the user.

1.3 Port and Identification Module

The system 100 also includes a port 124 arranged on the garment 150 and an identification module configured to communicate garment-related data (e.g., type, thickness, transmittance of solar radiation, etc.) via the port 124 when an exposure-tracking module 110 engages the port 124. Generally, the port 124 functions as a physical interface between an exposure-tracking module 110 and the garment 150; and the identification module functions as a data or identification interface between the exposure-tracking module 110 and the garment 150.

In various implementations, the port 124 can include: a set of mechanical snap buttons configured to transiently engage and retain an exposure-tracking module 110; a set of magnetic elements configured to transiently engage and retain ferro-magnetic elements in an exposure-tracking module 110; or a threaded element and locking feature configured to transiently mate with and lock to complementary features on an exposure-tracking module 110. However, the port 124 can define any other form or feature configured to transiently engage and retain an exposure-tracking module 110 against the garment 150.

In one example in which the garment 150 defines a cycling, football, or soccer jersey, the port 124 can be arranged on the back of the jersey at the base of the jersey's collar; when an exposure-tracking module 110 is attached to the port 124, the port 124 can thus locate the exposure-tracking module 110 near a user's neck, which may represent a common high-Sun-exposure area for these sports such that incident solar radiation data collected by the exposure-tracking module 110 is representative of the user's true Sun exposure. In a similar example in which the garment 150 defines a short-sleeved running jersey, the port 124 can be arranged on the left (or right) sleeve of the jersey; when an exposure-tracking module 110 is attached to the port 124, the port 124 can thus locate the exposure-tracking module 110 near a user's left upper arm, which may represent a common high-Sun-exposure area for runners such that incident solar radiation data collected by the exposure-tracking module 110 is representative of the user's true Sun exposure. In another example in which the garment 150 defines a ski coat, the port 124 can be arranged on a breast pocket of the ski coat; when an exposure-tracking module 110 is attached to the port 124, the port 124 can thus locate the exposure-tracking module 110 over a user's chest and near the user's face, which may represent the region of the user's body most susceptible to ultraviolet exposure such that incident solar radiation data collected by the exposure-tracking module 110 is representative of the user's true Sun exposure. However, the port 124 can be arranged on or integrated into the garment 150 at any other generic, sport-relative, or activity-specific location.

The port 124 thus enables the garment 150 to be separated from an exposure-tracking module 110. To enable the same or other exposure-tracking module 110 to pair incident solar radiation data collected during a session with garment-related data that the software program can then merge into a precise (i.e., accurate and repeatable) estimation of a user's true ultraviolet exposure during the session, the identification module can store identification information for the garment 150; upon receipt of a query from an exposure-tracking module 110 installed over the port 124, the identification module can return this identification to the exposure-tracking module 110 via the port 124.

In one implementation, the identification module includes an ID chip preloaded with a substantially unique identifier or ("UUID") and is electrically coupled to a set of prongs, pads, or other electrical interfaces in the port 124; when the exposure-tracking module 110 is connected to the port 124, electrical connections in the exposure-tracking module 110 mate with the corresponding prongs, pads, or other electrical interfaces in the port 124 to enable the exposure-tracking module 110 to communicate with the identification module. For example, the identification module can be connected to each of a ground, power, and one data pin arranged in the port 124; when connected to the port 124 the exposure-tracking module 110 can ground the ground pin, supply power to the power pin, and transmit and receive data to and from the identification module over the data pin via I2C communication protocol. Upon receipt of a unique ID from the identification module, the exposure-tracking module 110 can pair solar radiation data collected during the current session with this unique ID and upload these data to a local computing device and/or to a remote server. The local computing device or remote server can then pass the unique ID through a name mapping system 100 to retrieve garment-related data and then process these incident ultraviolet radiation solar radiation data into an ultraviolet exposure level for the user, as described below.

In another implementation, the identification module includes an ID chip preloaded with garment-related data. For example, the identification module can be preloaded with: body areas covered by the garment 150 (e.g., torso, upper arm, and/or lower arm); or a percentage of torso and upper limb skin area covered by the garment 150 (e.g., 55% for a sleeveless jersey or 85% for a long-sleeved jersey). The identification module can also be preloaded with body areas or body area proportions covered by other items commonly worn with the garment 150, such as by a helmet with the garment 150 defining a football jersey or cycling shorts and socks for the garment 150 defining a cycling jersey.) The identification module can also be loaded with a size of the garment 150 (e.g., small, medium, or large, etc.); and the software program can estimate the user's total skin area based on the size of the garment 150 and a predefined skin area model.

Furthermore, the identification module can also be preloaded with a total solar rejection ratio or UV-A, UV-B, UV-C, visible light, and IR rejection ratios of the garment's material (e.g., 90%, 95%, or 98%), such as in the form of a UPF or SPF rating of the garment's material.

Additionally or alternatively, the identification module can be preloaded with a solar reflectance value of a ground covering common to a sport or activity performed while wearing the garment 150, such as a total solar reflectance value or UV-A, UV-B, and UV-C reflectance values of grass for the garment 150 that defines a soccer or football jersey, of asphalt for the garment 150 that defines a running or cycling jersey, or of snow for the garment 150 that defines a skiing coat. The identification module can thus serve these data to the exposure-tracking module 110 when the exposure-tracking module 110 is installed on the garment 150 to enable the exposure-tracking module 110 to locally transform incident solar radiation data into a total ultraviolet exposure of the user. However, the identification module can be preloaded with any other user- or garment-related data. Alternatively, the ID stored in the identification module can be linked to any of the foregoing data, such as in a remote database via a name mapping system, as described above.

1.4 Exposure-tracking module

As shown in FIG. 1, the exposure-tracking module 110: is configured to transiently couple to the port 124 via a jack 114; is configured to read the identifier of the garment 150 from the identification module; and includes a radiation sensor 116 configured to detect levels of incident solar radiation (e.g., IR, visible and/or ultra-violet light). Generally, the exposure-tracking module 110 defines an electronic module that can be transiently connected to one of any number of ID-enabled garments to collect incident solar radiation data during a training session.

In one implementation, the exposure tracking module includes: a housing 112 configured to transiently attach to the port 124 on the garment 150; a jack 114 coupled to the housing 112 configured to transiently engage a port 124 on the garment 150; a radiation sensor 116 arranged in the housing 112 and configured to detect solar radiation incident on the housing 112; and a controller 130.

In the foregoing implementation, the exposure-tracking module 110 includes: a housing 112, such as a plastic injection-molded and silicone over-molded housing 112. The housing 112 can define an outer surface and a jack 114—opposite the outer surface—configured to engage (e.g., insert into) the port 124 in an ID-enabled garment 150. For example, the jack 114 can include a ferrous prong configured to mate with a complimentary port 124 of the smart-garment 150. Similarly, the jack 114 can be configured to mate with the port 124 with a snap feature, a threaded feature, or any other transient connection means. In this implementation, the housing 112 can include a seal configured to resist influx of liquids, such as water, and protect internal components from damage. The exposure-tracking module 110 can also include a radiation sensor 116, such as a digital UV Index light sensor, adjacent an UV-transparent region of the outer surface of the housing 112.

In another implementation, the exposure-tracking module 110 can include local memory arranged in the housing 112; and a controller 130 arranged in the housing 112 and configured to sample the radiation sensor 116, to read an identifier from an identification module in a connected garment 150, and to store incident solar radiation data and the identifier to memory. In this implementation, the exposure-tracking module 110 can sample solar radiation data from the radiation sensor 116 and store the solar radiation data locally in the local memory.

Furthermore, the exposure-tracking module 110 can include a wireless communication module arranged in the housing 112 and configured to transmit solar radiation data and the identifier to a local computing device, such as in real-time, intermittently (e.g., once per two-minute interval), or asynchronously (e.g., at the conclusion of a training session); and a rechargeable battery arranged in the housing 112 configured to power the controller 130 and the wireless communication module.

Because the garment-related data is linked to the garment 150 or stored on the garment 150 itself (e.g., rather than stored on the exposure-tracking module 110), the exposure-tracking module 110 can be connected to multiple ID-enabled garments over time while also enabling the software program—which may execute locally on the exposure-tracking module 110, on a separate mobile computing device, or remotely at a remote server—to access both incident solar radiation data from the exposure-tracking module 110 and garment-related data that informs transformation of these incident solar radiation data into an accurate estimation of the user's ultraviolet exposure during a training session. For example, a user may own or be provided (e.g., by a team) one exposure-tracking module 110 and multiple ID-enabled garments, such as one sleeveless, one short-sleeved, and one long-sleeved ID-enabled garment 150, as shown in FIG. 2. The user can: connect the exposure-tracking module 110 to the sleeveless garment 150 and wear the sleeveless garment 150 during a hot-weather session; connect the exposure-tracking module 110 to the short-sleeved garment 150 and wear the short-sleeved garment 150 during a warm-weather session; and connect the exposure-tracking module 110 to the long-sleeved garment 150 and wear the long-sleeved garment 150 during a cold-weather session. In these examples, the exposure-tracking module 110 can access a unique ID from an identification module in the connected garment 150 and pair this unique ID with incident solar radiation data collected during each corresponding session; by accessing garment-related data related to these unique IDs, the software program can track the user's ultraviolet exposure during each of these sessions, which may be a function of the garment's material, the garment's coverage, and a ground covering near the user during each session. The user can then separate the exposure-tracking module 110 from a garment 150 in order to recharge the battery within the exposure-tracking module 110, synchronize the module with a remote computer or device, update the module's firmware programing, and/or wash the garment 150.

The exposure-tracking module 110 can also include a motion sensor, such as an accelerometer, a compass sensor, and/or a tilt sensor, and/or orientation sensor configured to read orientation data of the exposure-tracking module 110. In one implementation, the controller 130 can thus transition from an inactive (e.g., "sleep" or "hibernate") mode to an active mode responsive to an output of the motion sensor and/or predict an activity of the user wearing the exposure-tracking module 110 based on a magnitude and/or frequency of outputs of the motion sensor. Additionally or alternatively, the controller 130 can selectively—and opportunistically—read solar radiation values from the radiation sensor 116 based on orientation of the exposure-tracking module 110. For example, the controller 130 can selectively sample the radiation sensor 116 when the exposure-tracking module 110 aligns with a target orientation of the exposure-tracking module 110 in which the radiation sensor 116 is directed in a particular direction, such as a direct, diffuse, and/or global direction as described in U.S. patent application Ser. No. 15/648,158, which is herein incorporated in its entirety by this reference.

Throughout operation (e.g., while in the active mode), the controller 130 can regularly sample the radiation sensor 116, such as once per minute or at a rate of 0.1 Hz, timestamp these data, and immediately transmit these data to a local computing device or store these data in memory for later transmission to the local computing device.

The exposure-tracking module 110 can additionally or alternatively include an ambient temperature sensor, a skin temperature sensor, a heart rate sensor, a respiratory rate sensor, an IR irradiance sensor, a visible light irradiance sensor, a barometer, altimeter, and/or any other ambient or biometric sensor; and the controller 130 can transition from the inactive mode to the active mode and/or track biometric signals of the user based on outputs of these sensors. For example, a user's skin temperature may be proportional to both solar radiation exposure and ambient air temperature. Therefore, the software program can: track ambient air temperature through a temperature sensor integrated into the exposure-tracking module 110; and increase solar radiation exposure threshold for the user as an inverse function of ambient air temperature, and vice versa. Similarly, the software program can: track the user's skin temperature through a skin temperature sensor integrated into the garment 150; and increase solar radiation exposure threshold for the user as an inverse function of ambient air temperature, and vice versa.

Therefore, the software program can predict athletic performance effects based any one or more of: solar radiation levels; solar radiation levels; exposed skin area; skin temperature; ambient air temperatures; humidity; duration of exposure; and/or other biometric values (e.g., heart rate, respiratory rate, etc.); etc. of the user and the user's environment and can serve real-time and/or asynchronous prompts to the user accordingly. However, the exposure-tracking module 110 can be of any other form and include any other active or passive components.

2. Method

As shown in FIG. 1, a method S100 for tracking and responding to ultraviolet exposure includes: reading an identifier of a garment 150 worn by a user in Block S110; estimating the skin exposure of a user wearing the garment 150 based on the identifier in Block S120; at a first time, reading an solar radiation value from a radiation sensor 116 transiently coupled to the garment 150 in Block S130; and, based on the solar radiation value and the skin exposure, estimating an ultraviolet exposure of the user at the first time in Block S140.

Generally, the controller 130 executing the software program is configured: to access a type of the garment 150 based on the identifier of the garment 150; to estimate levels of solar radiation exposure on the user's skin based on the type of the garment 150 and levels of incident solar radiation (e.g., ultra-violet light, visible light, infrared light, etc.) detected by the exposure tracking radiation sensor 116 over time; and to serve a prompt to the user to reduce exposure in response to an estimated level of exposure on the user's skin exceeding a threshold. The software program can be implemented entirely or in part at the exposure-tracking module 110, at a native exposure-tracking application on the user's (or a coaches, etc.) mobile computing device, and/or at a remote server to transform garment-related data and incident solar radiation data collected by the exposure-tracking module 110 during a training session into the user's solar radiation exposure and to notify the user (or the coach, etc.) of current or predicted over-exposure that may reduce the user's performance.

2.1 Garment Identifier

Block S110 of the method 5100 recites reading an identifier of a garment 150 worn by a user in Block S100. Generally, the software program can access the identifier of the garment 150 (e.g., a unique ID), which can include specification of the type of garment 150, material, solar rejection ratio, etc., from the port 124 of the garment 150 via the jack 114 coupled to the housing 112. The software program can query the identification module of the garment 150 for the identifier and the identifier module can transmit the identifier through the port 124 of the garment 150 and the jack 114 coupled and the housing 112 to the controller 130 of the exposure-tracking module 110.

In one implementation, upon receipt of the unique ID from the identification module in the garment 150, the software program queries a name mapping system 100 (e.g., stored on the exposure-tracking module 110, in a native exposure-tracking application executing on the user's computing device, or on a computer network) for garment-related data, as described above.

2.2 Skin Exposure

Block S120 of the method S100 recites estimating the skin exposure of a user wearing the garment 150 based on the unique ID. Generally, the software program can read the unique ID, retrieve a geometry and/or estimated skin coverage of the garment 150 based on the unique ID, and calculate an amount (or proportion) of the user's skin exposed to solar radiation (i.e., and uncovered by the garment 150 and/or other complimentary garments).

In one implementation, the software program can read the unique ID of the garment 150 and query the NMS for geometry information of the garment 150, such as size, shape (e.g., long-sleeved, short-sleeved, sleeveless), and/or estimated percentage of an average user's skin covered by the garment 150. Based on the geometry information, the software program can estimate a proportion of the user's skin exposed to sunlight and a proportion of the user's skin covered by the garment 150. Alternatively, the software program can estimate an absolute skin surface area exposed to sunlight and uncovered by the garment 150.

In another implementation, the software program can prompt the user to enter her height and weight through a user portal. Based on her height and weight, the software program can calculate a total skin area of the user. The software program can then access geometry data of the garment—corresponding to the unique ID of the garment—and estimate the skin surface area covered by the garment when the user is wearing the garment. Based on the total skin area of the user and the skin surface area covered by the garment, the software program can calculate the skin exposure as a difference between the total skin area and the skin surface area covered by the garment.

In one variation, the software program can read the unique ID of the garment 150 and query a lookup database for a (probable) set of complementary garments likely worn by the user while wearing the smart-garment 150. The software program can then estimate a skin exposure based on an estimated proportion of the user's skin exposed to direct Sunlight and uncovered by both the garment 150 and the set of complementary garments. For example, the user may wear a smart cycling jersey with the port 124 configured to accept the exposure-tracking module 110. In this example, while wearing the smart cycling jersey, the user may wear a (non-smart) helmet, cycling shorts, cycling socks, and/or gloves. At a lookup database, the system 100 can store possible (and probable) combinations of clothing complementary to the smart-garment 150 likely to be worn when wearing the smart-garment 150. Therefore, the software program can query the lookup database for additional and complementary garments worn by the user while wearing the smart-garment 150 and the lookup database can return the set of complementary garments (e.g., helmet, cycling shorts, cycling socks, and/or gloves). Additionally or alternatively, the software program can query a user to input complementary garments worn simultaneously with the smart garment 150 and store this information for future reference. The software program can then access garment 150 information of the complementary garments (e.g., skin coverage information, geometry, or solar rejection ratio) and adjust the skin exposure to account for all garments worn by the user simultaneously.

However, the software program can calculate the skin exposure in any other suitable way.

2.3 Solar Radiation Data

Block S130 of the method recites, at a first time, reading a solar radiation value from a radiation sensor 116 transiently coupled to the garment 150. Generally, the controller 130 can sample the radiation sensor 116 regularly and/or intermittently to record solar radiation data.

In one variation, the exposure-tracking module 110 can: read a sequence of ultraviolet values from the ultraviolet sensor as the exposure-tracking module 110 sweeps through the orientation window, such as at a rate of 10 Hz; and then store a singular maximum solar radiation value in this sequence of ultraviolet values as the solar radiation value for this sampling interval.

In another variation, in response to detecting alignment between orientation of the exposure-tracking module 110 and a target orientation at approximately the current time (or within a sampling interval succeeding the first time), the method S100 can be implemented to record a first solar radiation value. The exposure-tracking module 110 can: regularly sample (e.g., at a rate of 10 Hz) orientation sensors integrated into the exposure-tracking module 110 to determine the orientation of the ultraviolet exposure-tracking module 110 relative to a reference frame; read an solar radiation value from the ultraviolet sensor when alignment between the detected orientation of the exposure-tracking module 110 falls within a tolerance of a target orientation (or within a target orientation window) calculated for the current sampling interval; and then store this solar radiation value (e.g., an ultraviolet irradiance value in Watts per square meter) for this sampling interval.

Similarly, the exposure-tracking module 110 can: read a sequence of ultraviolet values from the ultraviolet sensor as the exposure-tracking module 110 sweeps through the orientation window, such as at a rate of 10 Hz; tag each solar radiation value in this sequence with an orientation of the exposure-tracking module 110 relative to the reference frame; and then store a singular solar radiation value in this sequence of ultraviolet values tagged with an orientation nearest a target orientation as the solar radiation value for this sampling interval.

Alternatively, the exposure-tracking module 110 can: record a first solar radiation value read from the ultraviolet sensor once the exposure-tracking module 110 enters an initial orientation window (e.g., defined by a 15° cone axially aligned with a target orientation); recalculate a second, tighter orientation window (e.g., defined by a 10° cone axially aligned with a target orientation); replace the first solar radiation value with a second solar radiation value read from the ultraviolet sensor once the exposure-tracking module 110 enters the second orientation window; recalculate a third, tighter orientation window (e.g., defined by a 5° cone axially aligned with a target orientation); replace the second solar radiation value with a third solar radiation value read from the ultraviolet sensor once the exposure-tracking module 110 enters the third orientation window; etc. during the sampling interval, thereby refining and increasing accuracy of an solar radiation value recorded for this sampling interval, as described below.

2.3.1 Opportunistic Readings

In one variation of the method, the exposure-tracking module 110 can opportunistically record ultraviolet values when target conditions defined by the exposure-tracking module 110 are met, such as when inadvertent movement of the exposure-tracking module 110 by the user aligns its integrated ultraviolet sensor to precalculated direct, diffuse, and/or global orientations, thereby reducing or eliminating a need for the user to manually and intentionally orient the exposure-tracking module 110 in preparation for such readings, which may otherwise frustrate the user, limit use of the exposure-tracking module 110 over time, and reduce accuracy of the user's ultraviolet exposure calculated by the exposure-tracking module 110 over time due to low repeatability and high degrees of error in manual positioning of the exposure-tracking module 110 by a user.

In one implementation, orientation sensors (e.g., a multi-axis gyroscope, compass, accelerometer, and/or tilt sensor) integrated into the exposure-tracking module 110 can output yaw, pitch, and roll orientations of the light exposure device, such as relative to the reference frame of the Earth or relative to an arbitrarily-defined reference frame. For example, the exposure-tracking module 110 can include a compass sensor, a multi-axis tilt sensor or accelerometer, and a multi-axis gyroscopic sensor; and the exposure-tracking module 110 can fuse an absolute compass direction output by the compass, angular velocity values output by the gyroscopic sensor, and acceleration values output by the tilt sensor or accelerometer into a pitch, yaw, and roll position of the exposure-tracking module 110 relative an Earth reference frame per sampling interval. From the solar position, the exposure-tracking module 110 can define a target direct orientation for the light exposure device, such that, when outputs of these sensors indicate that the exposure-tracking module 110 is aligned with the target direct orientation, an ultraviolet sensor integrated into the exposure-tracking module 110 is directed parallel to the incident radiation from the Sun.

In particular, rather than prompting a user wearing (or carrying) the exposure-tracking module 110 to manually align the exposure-tracking module 110 with the target direct orientation during a sampling interval, the exposure-tracking module 110 can: intermittently wake from a sleep state to collect ultraviolet data (e.g., once per fifteen-minute interval); define target direct, diffuse, and/or global orientations for collection of ultraviolet values during this interval; regularly sample the orientation sensors during this interval to monitor the orientation of the light exposure device; automatically record ultraviolet values from the ultraviolet sensor in response to the orientation of the exposure-tracking module 110 falling within a threshold difference from each of the target direct orientation, the target diffuse orientation, and/or the global orientation; transform these ultraviolet values into an solar radiation exposure value for the user for this interval; and then return to the sleep state. The exposure-tracking module 110 can repeat this cycle over time, such as during known daylight hours for the current date and location of the light exposure device, and aggregate solar radiation exposure values for each interval during a single day into a cumulative solar radiation exposure value for the user for this day.

For example, the user may rotate the exposure-tracking module 110 into the target global orientation while opening a door or performing any other task; in response to detecting that its orientation has fallen within a threshold difference of the target direct orientation (or a range of direct orientations) for the current time of day, date, and approximate geolocation of the light exposure device, the exposure-tracking module 110 can record a global ultraviolet value. The exposure-tracking module 110 can similarly record ultraviolet values when the detected orientation of the exposure-tracking module 110 falls within threshold differences of the target direct and diffuse orientations. (However, the exposure-tracking module 110 can opportunistically collect ultraviolet data for other target orientations of the exposure-tracking module 110 based on predicted positions of the Sun relative to Earth at corresponding times of day, days of the year, and locations stored on the light exposure device.)

As shown in FIG. 2, the exposure-tracking module 110 can also include an ambient light sensor configured to output a signal corresponding to a level of incident ambient (visible) light and arranged proximal the ultraviolet sensor in the light exposure device. For example, in response to lack of a signal from the ambient light sensor during known daylight hours at the current time and location of the light exposure device, the exposure-tracking module 110 can determine that the ambient light sensor is obscured, such as by a sleeve covering a wrist on which the exposure-tracking module 110 is worn by a user. Because the ambient light sensor is adjacent the ultraviolet sensor, obfuscation of the ambient light sensor may indicate similar obstruction of the ultraviolet sensor. Therefore, the exposure-tracking module 110 can postpone or cancel collection of ultraviolet data during a current sampling interval while the ambient light sensor is obstructed, thereby avoiding recordation of aberrant or irrelevant ultraviolet values when conditions surrounding the ultraviolet sensor are unfavorable to collection of accurate sensor data.

In the foregoing example, the exposure-tracking module 110 can also detect presence of ambient light based on an output of the ambient light sensor, confirm that the ambient light and ultraviolet sensors are not obscured, and then enable collection of ultraviolet data through the ultraviolet sensor. (Similarly, the exposure-tracking module 110 can concurrently sample the ambient light sensor and the ultraviolet sensor when the exposure-tracking module 110 aligns with a target orientation and then retroactively confirm that the ultraviolet sensor was not obscured during this sampling interval based on an ambient light level read from the ambient light sensor during this same sampling interval.) However, in response to detecting the presence of ambient light but little or no solar radiation (e.g., UVB specifically, which may penetrate fused silica and fused quartz but may not penetrate other common glasses), the exposure-tracking module 110 can determine that it is located indoors and estimate the user's solar radiation exposure at null until an increase in detected incident solar radiation—indicating that the exposure-tracking module 110 is outdoors—is recorded.

Furthermore, the ambient light sensor can cooperate with the ultraviolet sensor to prioritize target orientations for recording ultraviolet values. For example, in response to detecting the presence of ambient light, the exposure-tracking module 110 can record a direct solar radiation value in response to detecting its alignment with the target direct orientation, a diffuse solar radiation value in response to detecting its alignment with the target diffuse orientation, and a global solar radiation value in response to detecting its alignment with the target global orientation. In this example, the exposure-tracking module 110 can determine that the direct solar radiation value corresponds to an ultraviolet index significantly less than ultraviolet indices corresponding to the global and diffuse ultraviolet values. Thus, the exposure-tracking module 110 can determine that its location is outside yet away from direct sunlight, such as in a shaded area or under overcast skies, and can temporarily reject direct ultraviolet values recorded by the ultraviolet sensor, thereby applying the direct and diffuse ultraviolet values to calculate a current ultraviolet index based on shade or cloudy sky ultraviolet exposure models and algorithms.

Alternatively, the exposure-tracking module 110 can determine that the incident solar radiation value corresponds to cumulative erythemal dose including: a standard erythemal dose—defined as a erythemally-weighted UV irradiation—and a minimum erythemal dose—defined as an amount of weighted UV irradiance that cause the user's skin to turn red (this is different for every skin type).

2.4 Solar Radiation Exposure

Block S140 of the method recites, based on the solar radiation value and the skin exposure, estimating an ultraviolet exposure of the user at the first time. Generally, the software program can calculate an approximate ultraviolet exposure of the user that accounts for incident solar radiation as well as skin coverage by the garment 150.

Upon receipt of garment-related data, the software program can populate a parametric ultraviolet exposure model with: the skin exposure (e.g., skin area coverage proportion for the garment 150); UV-A, UV-B, UV-C, visible, and IR light rejection ratios for the garment's material; skin area coverage and UV-A, UV-B, UV-C, visible, and IR light rejection ratios for other clothing articles commonly worn with the garment 150 (e.g., cycling shorts and a helmet with a cycling jersey, shorts with a running jersey, etc.); a predefined correction factor for the location of the port 124 on the garment 150 (e.g., "1.0" for the port 124 located at the base of the neck; "1.4" for the port 124 located at the lower edge of the flank of the garment 150; and/or an ambient reflectance value common to surfaces associated with the type of garment 150; etc. The software program can then: pass an incident solar radiation value—recorded by the exposure-tracking module 110—to calculate an ultraviolet exposure value for the corresponding instant in time; and integrate these ultraviolet exposure values over time based on a known sampling rate or known time between sampling periods at the exposure-tracking module 110 to estimate a total ultraviolet exposure on the user's skin during the current training session, such as in real-time as the incident solar radiation data is collected by the exposure-tracking module 110. The software program can thus estimate a total ultraviolet exposure on the user's skin; alternatively, the software program can implement the foregoing methods and techniques to estimate a total ultraviolet exposure on the user's skin in each of the UV-A, UV-B, and UV-C bands.

In a similar implementation, the software program accesses a solar radiation curve for the user's location; retrieves an incident solar radiation value recorded by the exposure-tracking module 110; calculates a position of the radiation sensor 116 relative to the Sun based on a time of day of recordation of the solar radiation value and a typical position of the radiation sensor 116 relative to the ground when installed on the garment 150 and worn by the user (e.g., based on the position of the port 124 on the garment 150 and the type of related activity); and then calibrates the solar radiation curve based on the incident solar radiation value and the position of the radiation sensor 116 relative to the Sun. The software program then integrates the solar radiation curve over a duration of time that the garment 150 is worn by the user. The software program can also: recalibrate the solar radiation curve upon receipt of a next solar radiation value from the exposure-tracking module 110 and based on a recordation time of this solar radiation value; and integrate this revised solar radiation curve over time going forward until a subsequent solar radiation value is receipt. The software program can repeat this process until conclusion of the current activity session in order to estimate a total ultraviolet exposure on the user's skin.

In the foregoing implementation, the software program can also interface with the native ultraviolet exposure application to receive confirmation from the user that she has applied Sunscreen prior to and/or during the session, the type of Sunscreen applied, and where the Sunscreen was applied. The software program can pass these data into the parametric ultraviolet exposure model to compensate for Sunscreen applied by the user and to thus further improve accuracy of the estimated total ultraviolet exposure of the user.

The software program can also access a generic threshold maximum ultraviolet exposure or a threshold maximum ultraviolet exposure selected by the user (or a coach, etc.), such as through the native ultraviolet exposure application executing on the user's computing device and stored in the user's (or a teams') account. Alternatively, the software program can access the user's total ultraviolet exposure and performance data collected automatically or entered manually by the user (or by a coach, etc.) during previous sessions and can calculate a threshold maximum ultraviolet exposure—that accounts for the user's estimated resilience to ultraviolet exposure (e.g., based on the user's position on a skin tone scale)—for the user's current session based on these data. For example, the software program can select or calculate a threshold maximum ultraviolet exposure in the form of an irradiance (e.g., "Watt/$m^2$") value, dosage (e.g., "Joules/$m^2$," or irradiance integrated over time), or energy (e.g., "Joules") for each of UV-A, UV-B, and UV-C.

The software program can then trigger an alarm when the estimated total ultraviolet exposure on the user's skin exceeds the threshold maximum ultraviolet exposure selected or calculated for the current session. In one example in which the software program executes on the exposure-tracking module 110, the software program can trigger the exposure-tracking module 110 to activate an internal buzzer and/or activate an integrated vibrator. The software program can additionally or alternatively broadcast a notification to a paired mobile computing device (e.g., a smartphone or smartwatch associated with the user, a coach, etc.), such as a notification suggesting that the user seek immediate shade, cease the current exercise, apply Sunscreen, or don an additional layer of clothing, as described below.

The software program can also: calculate a trend (e.g., a parametric time-based trendline, a time-series analysis generated with a predictive model) in the total ultraviolet exposure on the user's skin over time (e.g., since the beginning of the current session); extrapolate total ultraviolet exposure on the user's skin into the future based on this trend; and compare this extrapolated trend to the threshold maximum ultraviolet exposure for the current session to predict whether and when the user's total ultraviolet exposure will exceed the threshold maximum Sun exposure. Thus, if the extrapolated trend suggests that the user's total exposure will exceed the threshold maximum ultraviolet exposure within a threshold period of time (e.g., within the next 20 minutes), before the scheduled conclusion of the current session, or before the predicted conclusion of the current session (e.g., based on durations of past sessions by the user with the same garment 150 or other ID-enabled garments of the same type), the software program can issue a notification through the user's mobile computing device or through the exposure-tracking module 110 in real-time to prompt the user to adjust the current training session in order to limit her total Sun exposure, which may reduce the user's recovery time following the current session.

The software program can implement similar methods and techniques to: select or calculate a maximum ultraviolet exposure rate, such as in the form of an irradiance (e.g., "Watt/$m^2$") value; extract a rate of ultraviolet exposure from the trend in total ultraviolet exposure on the user's skin; and prompt the user (or the coach, etc.) to adjust the current training session in order to reduce her rate of ultraviolet exposure if the current rate of ultraviolet exposure exceeds the threshold ultraviolet exposure rate. For example, the software program can prompt the user to apply Sunscreen, don an additional layer of clothing, complete the current session indoors or in a shaded outdoor area, or adjust the training schedule for a time when the solar irradiance is at a target level in order to extend the user's time to exhaustion as shown in FIGS. 5A and 5B.

The software program can implement the foregoing methods and techniques substantially in real time in order to provide the user (or the coach, etc.) with real-time feedback and guidance related to the user's ultraviolet exposure in order to extend the user's time to exhaustion and/or to reduce the user's recovery time following the current training session. Alternatively, the software program can implement the foregoing methods and techniques asynchronously—such as when the user downloads data from the exposure-tracking module 110 to her smartphone upon conclusion of the current training session—in order to inform the user when and how to adjust her future training sessions to reduce total ultraviolet exposure and ultraviolet exposure rate, which may extend the user's time to exhaustion and/or reduce the user's recovery time following future training sessions.

Therefore, the software program can collect or estimate any of the following before, during, and/or after a training session: time, date, location, height, weight, skin type, age, proportion of skin exposed, solar radiation rejection (e.g., by Sunscreen and/or clothing), planned or actual ultraviolet exposure time, planned or actual solar radiation exposure time, target vitamin D synthesis, and/or UV index, etc. for the user. The software program can transform these data into: local Sun altitude angle, local Sun azimuth angle, estimated UV index, UV index curve for a period of time (e.g., one day), time to Sunburn, time to reach vitamin D synthesis target, amount of synthesized vitamin D, minimum suggested exposed skin area % to reach vitamin D target (E.g., before Sun burn), reduction in athletic endurance, etc. for the user.

However, the software program can process incident solar radiation (e.g., UV, visible, and/or IR light) data collected by the exposure-tracking module 110 and provide related guidance to the user (or to a coach, etc.) in any other way or according to any other schema.

2.5 Posture

In one variation, the software program can read the unique ID of the garment and access a lookup table to predict a type of activity performed by the user while wearing the garment 150. Based on the type of activity, the software program can predict a posture (or body position) of the user while wearing the garment 150. From this posture, the software program can estimate an orientation of the radiation sensor 116 relative to a target orientation (e.g., direct, diffuse, or global). Furthermore, the software program can identify whether the radiation sensor 116 is obscured. For example, for an exposure-tracking module 110 connected to a port 124 on a front side of a cycling jersey, the software program can determine that the radiation sensor 116 is likely directed downward and away from the Sun. Therefore, the software program can selectively disable sampling of the radiation sensor 116. Additionally or alternatively, the software program can determine that readings from the radiation sensor 116 are likely diffuse solar radiation values and, as described above, adjust the diffuse solar radiation value according to the ultraviolet exposure model to define an overall ultraviolet exposure. Therefore, based on a predicted posture of the user, the software program can estimate an orientation of the exposure-tracking module 110, calculate an orientation of the radiation sensor 116 relative to a direct orientation (i.e., directly toward the Sun as predicted by a solar position model), and correct solar radiation values based on the known orientation of the radiation sensor 116.

Figure 6:
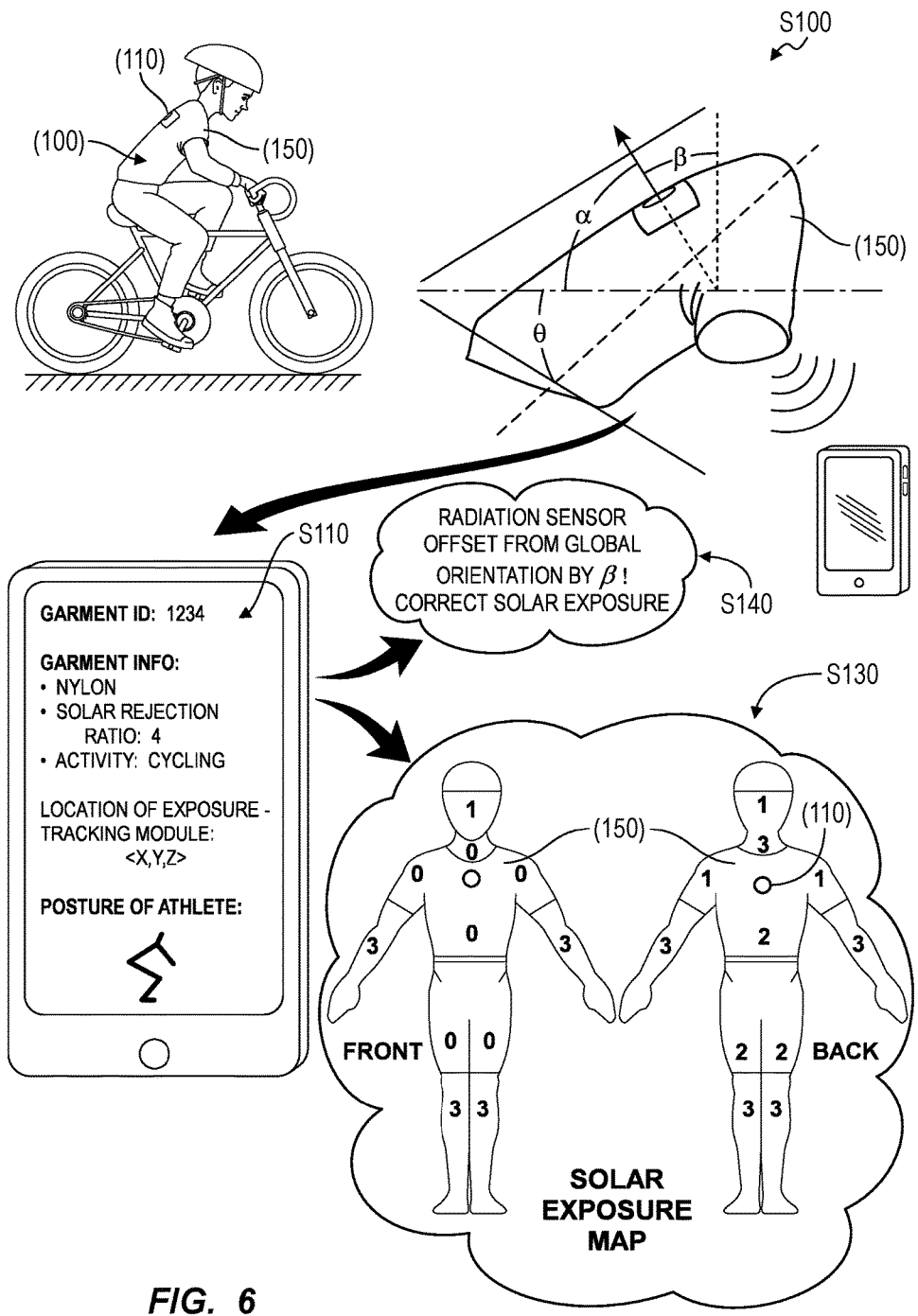
FIG. 6 is a flowchart representation of one variation of the method.

Furthermore, as shown in FIG. 6, the software program can apply the posture to generate an solar radiation distribution model that describes distribution of solar radiation over the user while the user is wearing the garment 150 based on the posture. In the foregoing example, a cyclist may experience greater solar radiation exposure at the back of her neck than at the front of her neck, on her face, and/or on the back of her legs. The software program can access a solar position based on a Solar position model, which describes the location of the Sun in the sky at a particular time, date, and location. Based on the posture and the solar position, the software program can predict shadows and solar radiation exposure over the cyclist's body, thereby defining an ultraviolet distribution model. Based on this model, the software program can adjust the ultraviolet exposure to adjust for uneven distribution of ultraviolet exposure over the cyclist's body while cycling.

3. Individual Users

Figure 3:
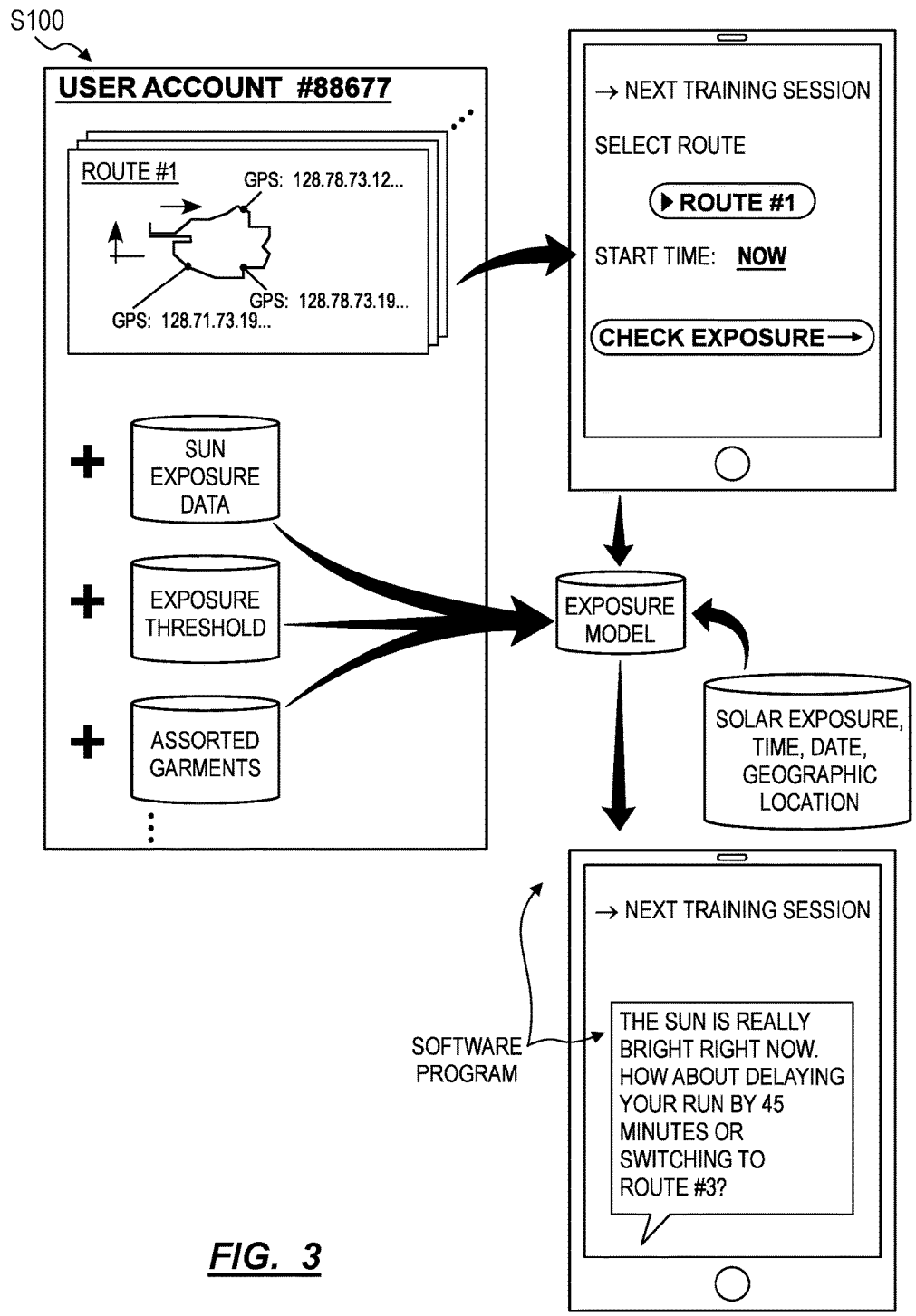
FIG. 3 is a flowchart representation of one variation of the system.

In one variation shown in FIG. 3, the system 100 is implemented to track a single user's (or athlete's) Sun exposure, prompt the user to adjust her training schedule in order to extend time to exhaustion and/or reduce recovery time following training sessions, and/or assist the user in planning upcoming training sessions to compensate for UV index forecasts, etc. Generally, in this variation, the system 100 can collect unique ID from the garment and incident solar radiation data from the exposure-tracking module 110, transform these data into UV, IR, visible light, and/or total ultraviolet exposure values for the user, and then provide guidance to the user in real-time, after the training session, or before a next training session in order to provide quantitative metrics enabling the user to affect her time to exhaustion and recovery time by controlling her ultraviolet exposure over time.

3.1 Ambient Reflectance

In this variation, the system 100 can measure or predict the ambient reflectance of a surface around the user during a training session based on one or more other sensor streams recorded at the exposure-tracking module 110. In one implementation, the exposure-tracking module 110 further contains an accelerometer; during operation, the controller 130 in the exposure-tracking module 110 samples the accelerometer, timestamps these acceleration data, and stores these acceleration data with incident solar radiation data. Upon receipt of these data, the software program can: identify the garment 150 as a cycling jersey based on a unique ID received from the identification module; retrieve a set of ambient reflectance values for ground surfaces common to cycling (e.g., asphalt, dirt, grass), each paired with an acceleration model; match acceleration data received from the exposure-tracking module 110 to one acceleration model; and then select a corresponding ambient reflectance value for the user during the current training session or segment of the current training session. For example, if these acceleration data exhibit relatively large-amplitude, regular oscillations, the software program can determine that the user is mountain biking and select an ambient reflectance model for dirt accordingly; similarly, if these acceleration data exhibit relatively small-amplitude, irregular oscillations, the software program can determine that the user is biking on a road surface and select an ambient reflectance model for asphalt accordingly.

In another example, the software program can identify the garment 150 as a running jersey and retrieve a set of ambient reflectance values for ground surfaces common to running (e.g., asphalt, dirt, grass, track), each paired with an acceleration model. If acceleration data received from the exposure-tracking module 110 indicates rapid accelerations and rapid motion over short periods of time, the software program can determine that the user is sprinting on a track and select an ambient reflectance model for a red track surface accordingly; similarly, if acceleration data received from the exposure-tracking module 110 indicates lower-amplitude accelerations over a longer period of time, the software program can determine that the user is running on asphalt and select an ambient reflectance model for asphalt accordingly.

The software program can then implement the selected ambient reflectance to predict the user's total Sun exposure, as described above. However, the software program can predict or determine surfaces near the user during the training session according to any other sensor stream recorded during operation of the exposure-tracking module 110.

3.2 Preloading Ambient Reflectance

In another implementation, the software program associates ambient reflectance values with various locations throughout a preplanned path of an upcoming training session. For example, the user can access a training planner within an instance of the native exposure-tracking application executing on her mobile computing device, as described above, access a map within the training planner, and then indicate waypoints within the map to define a new training route (e.g., a running path or a bike route) within the user's account. Alternatively, the native exposure-tracking application—executing on the user's smartphone or smartwatch, etc. carried by the user during a training session—can record GPS waypoints as the user traverses (e.g., runs or cycles along) a training route and then automatically define a new training route within the user's account based on these GPS waypoints. Later, the native exposure-tracking application can: prompt the user to name the new training route and to indicate prominent ground surface types—such as grass, asphalt, concrete, gravel, dirt, and/or track surface, etc.—along various segments of the training route; and then associate ambient reflectance values with segments of the training route based on these ground surface type labels provided by the user. Alternatively, the software program can automatically label segments of the training route: by projecting the training route onto a color geographical map; extracting colors from the map adjacent segments of the training route; associating these colors with prominent ground surface types, such as based on a lookup table; and then labeling segments of the training route accordingly.

In preparation for a training session at a later time, the native exposure-tracking application—executing the software program on a mobile computing device carried by the user—can: prompt the user to select a predefined training route from a set of training routes stored in the user's account; download location-based (e.g., GPS-tagged) ambient reflectance values for segments of the selected training route; and then implement the methods and techniques described above to estimate the user's total ultraviolet exposure during the training session based on incident Solar radiation data received from the exposure-tracking module 110 installed on a garment 150 worn by the user during the training session and based on GPS locations of the mobile computing device throughout the training session. (The native exposure-tracking application can also implement similar methods and techniques in real-time as the user traverses a new or known training route by referencing GPS locations of the user's mobile computing device against a color geographic map, as described above, or by referencing GPS locations of the user's mobile computing device against a geographic map labeled directly with local ambient reflectance values.) The native exposure-tracking application can thus calculate total ultraviolet exposure of the user with great accuracy by implementing dynamic, location-based ambient reflectance values.

Alternatively, the software program can: compile ambient reflectance values along the training route into one composite ambient reflectance, such as by calculating an average of these ambient reflectance values weighted according to the real length of corresponding segments of the training route, and then associate these composite ambient reflectance values with the training route. The software program—executing within the native exposure-tracking application on a mobile computing device carried by the user during the training session or executing locally on the exposure-tracking module 110—can then implement this composite ambient reflectance to calculate the user's total ultraviolet exposure during the training session.

The software program can then selectively prompt the user to seek shelter from the Sun, apply Sunscreen, or return home, etc. in real-time during the training session according to exposure-related triggers, as described above.

3.3 Predictive Ultraviolet Exposure Feedback

In another implementation, the software program can: access an average UV index and solar irradiance level over the duration and at the location of a training route previously completed by the user; retrieve incident solar radiation and solar radiation data collected by the exposure-tracking module 110 during this previous training session; normalize these incident solar radiation data according to the average UV index and solar irradiance levels during the previous session; and associate these normalized incident solar radiation data within segments of the training route based on GPS data collected by the mobile computing device while the user traversed the training route. The software program can also calculate ambient reflectance coefficients along discrete segments of the training route based on relative magnitudes of incident ambient light—normalized according to the average UV index—detected by the exposure-tracking module 110. In this implementation, these normalized incident solar radiation values may reflect true ambient reflectance, shade (e.g., from trees), and other factors affecting ultraviolet exposure along segments of the training route. (The software program can implement similar methods and techniques to normalize incident solar radiation data according to UV indices at discrete locations along the training route in order to further improve accuracy of the user's total ultraviolet exposure during later training sessions along the same training route.)

In this implementation, in preparation for a next training session, the user can access the native exposure-tracking application (e.g., executing on her mobile computing device) to indicate a training route for a next training session, such as by selecting from a drop-down menu of preplanned paths previously defined by the user or recorded during previous training sessions, and to enter a scheduled time for the next training session, as shown in FIG. 3. The native exposure-tracking application can then: access a forecast UV index at or near the location of the selected training route at a time of the next training session; multiply normalized incident solar radiation values stored with the path by the current UV index to predict incident solar radiation levels at these locations along the selected training route; estimate the user's total incident solar radiation during the next training session by integrating these predicted incident solar radiation levels along the length or estimated time of the training session; and then correct the user's total incident solar radiation according to the type (e.g., body coverage afforded by) and the material of a garment 150 commonly worn by the user during such training sessions in order to the predict the user's total ultraviolet exposure over the course of training session.

In this implementation, if the user's predicted total ultraviolet exposure exceeds a first threshold corresponding to reduced performance (or Sunburn, etc.), the native exposure-tracking application can: prompt the user to apply Sunscreen of a particular SPF level predicted to reduce the user's predicted total ultraviolet exposure to below the first threshold; and/or prompt the user to wear an alternate garment 150, such as a long-sleeved jersey rather than a short-sleeved jersey or to wear a visor, during the next training session in order to reduce the user's predicted total ultraviolet exposure to below the first threshold.

However, if the user's predicted total ultraviolet exposure exceeds a second threshold (greater than the first threshold) corresponding to a total ultraviolet exposure that cannot be compensated for with Sunscreen or a reasonable change in clothing, the native exposure-tracking application can prompt the user to wait until later in the day or the next morning, when the UV index has decreased, to begin the training session. Alternatively, the native exposure-tracking application can prompt the user to select an alternate training route exhibiting greater shade—as indicated by normalized incident solar radiation values—for the next training session, such as if the user has indicated that she will begin the next training session soon or immediately. For example, the native exposure-tracking application can: implement the foregoing process to calculate a total ultraviolet exposure for each other training route defined in the user's account; and identify a second path (e.g., of a shorter length, extending across more grassy areas, or affording more shade) for which the user's predicted total ultraviolet exposure is reduced below the first and/or second thresholds; and prompt the user to traverse this second training route rather than the route initially selected.

In a similar implementation, the user indicates her preferred time window for completing an upcoming training session through the native exposure-tracking application; the software program—executing within the native exposure-tracking application—can implement the foregoing processes to suggest one or a set of predefined training routes that the user can complete within the time window while limiting her total ultraviolet exposure to less than the first and/or second threshold Sun exposures. Similarly, the user can select a training route within the native exposure-tracking application and the software program can implement the foregoing processes to calculate a soonest time the user can begin this next training session while limiting her total ultraviolet exposure to less than the first and/or second threshold Sun exposures, such as given apparel and a Sunscreen type also suggested by the native app or indicated by the user.

The system 100 (e.g., the garment 150, the exposure-tracking module 110, the software program, and/or the native exposure-tracking application, etc.) can also cooperate to track the user's total ultraviolet exposure throughout a training session and to selectively serve prompts to the user substantially in real-time to control her total ultraviolet exposure to levels that yield extended time to exhaustion and reduce recovery time. The system 100 can additionally or alternatively serve these prompts and related data to the user asynchronously (e.g., upon conclusion of a training session) in order to teach the user tools for tracking and managing her ultraviolet exposure throughout training sessions.

The foregoing methods and techniques can be similarly implemented in conjunction with other sports—such as golf, skiing, and horseback riding—and/or on behalf of players on a team.

3.4 Route Adaptation

In one variation, the software program can aggregate training routes across multiple users, store temporal and spatial solar radiation values (ultraviolet, visible and IR) with each training route based on exposure data collected from users traversing these training routes, and share these training routes and ultraviolet exposure values with the same and/or other users. By aggregating exposure readings along a route and applying an algorithm to compare these aggregated readings to expected and forecast solar radiation levels a predictive exposure map may be created for the specific route and for any given date and time, showing portions of a route that are highly exposed (e.g. along a hilltop) as well as portions that are shaded (e.g. through a wooded park). For example, the software program can enable users (near these routes) to view and select from their own or other training routes based on associated ultraviolet exposure indices. The software program can therefore network users and training routes across users based on solar radiation exposure data. For example, the software program can prompt the user to enter a target ultraviolet exposure level per training session, per day, per week, per month, etc., or the software program can recommend such a target ultraviolet exposure level to the user. The software program can then suggest or automatically select a training route—from a set of training routes specific to the user or a set of training routes nearby aggregated from multiple users—for the user based on this target ultraviolet exposure level.

3.5 Examples

In one example, the user may attach the exposure module to a garment 150 by mating a jack of the exposure module to a port integrated into the garment. The software program can then determine that the exposure module is currently attached to the garment and, therefore, worn by a user. The controller can then ping (or otherwise wirelessly transmit confirmation to) a mobile computing device to confirm that the exposure module is attached to the garment. The mobile computing device can render a user portal (e.g., within a native application and/or window). The software program can then populate the user portal with the garment's unique ID. The software program can then query a NMS and/or other database to identify a type of activity performed by the user when wearing the garment corresponding to the garment's unique ID (e.g., a cycling jersey). Based on the type of activity, the software program can access a set of historical cycling routes ridden by the user in the past. Based on historical ultraviolet values recorded by the radiation sensor along the set of historical routes, the software program can calculate current erythemal indices at discrete points along each route in the set of historical routes. From these ultraviolet indices, the type of garment, estimated ground reflectance, average duration of the route in the past, etc., the software program can calculate an estimated cumulative ultraviolet exposure for each route in the set of historical routes of the user. Based on the estimated cumulative ultraviolet exposure, the software program can select a particular route or set of routes over which the estimated cumulative ultraviolet exposure falls below a threshold ultraviolet exposure. The software program can then render a suggestion to take the particular route (or set of routes) to the user within the native application. The user may then opt to take the particular route or elect an alternative route.

In a similar manner, the user may select a route based on predicted route-specific effects on athletic endurance. For example one user may select a route that is heavily shaded to minimize the reduction in his endurance due to solar radiation exposure in order to improve the musculoskeletal and cardiovascular benefits of the training session without becoming exhausted prematurely. Alternately, a second user may select an exposed route with high levels of solar radiation exposure to condition herself and improve her endurance and ability to compete in sunny conditions.

4. Team Sports

Figure 4:
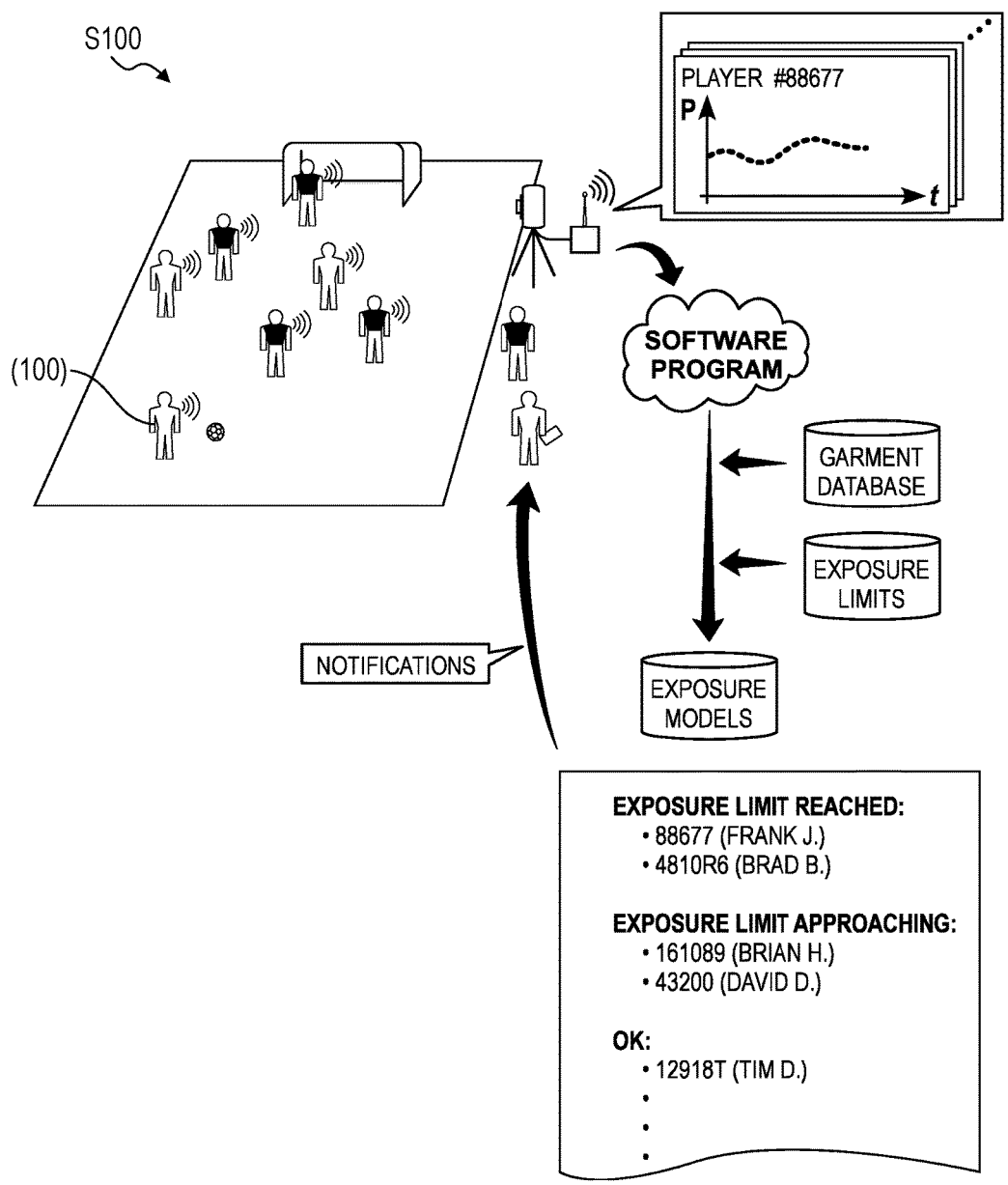
FIG. 4 is a flowchart representation of one variation of the system.

In one variation shown in FIG. 4, the system 100 is implemented in conjunction with an outdoor team sport, such as football, soccer, or baseball, in order to enable a coach (or an athletic director, a trainer, etc.) to track solar radiation exposure across players on the team, adjust a practice schedule in real-time in order to extend time to exhaustion and/or reduce recovery time for players on the team, and/or adjust an upcoming practice schedule to compensate for UV index and solar irradiation forecasts, etc.

4.1 Garment and Exposure-Tracking Module Distribution

In this variation, each player on the team can be provided with ID-enabled garments. For each garment 150, a unique ID encoded into the identification module in the garment 150 can be associated with one player on the team, such as in a name mapping system, to enable ultraviolet exposure of each player to be separately tracked. Each player can then "check out" one exposure-tracking module 110 prior to a practice session or competition. Alternatively, each player can be permanently assigned one exposure-tracking module 110, and a unique ID encoded into the exposure-tracking module 110 can be uniquely assigned to a corresponding player in the name mapping system.

4.2 Ultraviolet Exposure Limits

In this variation, generic threshold maximum ultraviolet exposure (e.g., "solar radiation dose") or generic threshold maximum ultraviolet exposure rates (e.g., "solar radiation dose rate") can be assigned to all players on the team. Alternatively, the coach (or trainer, etc. affiliated with the team) can assign custom threshold maximum Sun exposures and/or custom threshold maximum ultraviolet exposure rates to select players or groups of players, such as through a coaching portal accessible through a web browser. For example, the coach can assign a low maximum ultraviolet exposure rate to a quarterback on the (football) team, a low maximum ultraviolet exposure rate to a player recovering from an illness, a moderate maximum ultraviolet exposure rate to a player recovering from an injury, and a high maximum ultraviolet exposure rate to the kicker on the team. The coach can similarly assign—and the software program can implement—maximum ultraviolet exposure thresholds based on whether a player is scheduled to play in an upcoming game or whether a player is scheduled to start or close in the upcoming game.

Furthermore, in preparation for an upcoming competition in a location with an high forecast UV index and/or solar irradiance levels, the software program can guide the coach in increasing generic or custom maximum Sun exposures and maximum ultraviolet exposure rates for players on the team during practice sessions prior to the competition, thereby enabling these players to acclimate to greater ultraviolet exposure levels during practice sessions leading up to the upcoming competition; the software program can thus modify triggers for serving exposure-related notifications to the coach based on these updated maximum Sun exposures and maximum ultraviolet exposure rates for the team. For example, the coach can enter a practice schedule and a game schedule—including times of day and locations—of the team's upcoming competitions through the coaching portal, and the software program can: retrieve forecast UV index and solar irradiation data at the times and locations of upcoming practices and competitions; predict total ultraviolet exposure of groups of players on the team during a next competition based on its corresponding forecast UV index and solar irradiance and the length of the competition; automatically calculate maximum Sun exposures and maximum ultraviolet exposure rates for the team for each upcoming practice before the next competition based on forecast UV indices and solar irradiances during upcoming practices in order to gradually acclimate players to predicted Sun exposures and ultraviolet exposure rates during the competition; and then prompt the coach to confirm these maximum Sun exposures and ultraviolet exposure rates. During upcoming competitions, the software program can serve exposure-related prompts to the coach according to these Sun exposures and ultraviolet exposure rates, as described below.

4.3 Real-time Guidance

In one implementation shown in FIG. 3, a hub placed on a field or mobile computing device (e.g., a tablet or a smartphone) carried by a coach or assistant: collects unique ID and incident solar radiation data from exposure-tracking modules installed on garments worn by players during a practice session; and then uploads these data to a remote server executing the software program. The software program can implement the foregoing methods and techniques to track individual ultraviolet exposure levels and ultraviolet exposure rates of players on the team throughout the practice session and can selectively return prompts to the coach or assistant, such as through the mobile computing device or other local computing device, to control ultraviolet exposure of certain players based on their assigned maximum Sun exposures or maximum ultraviolet exposure rates for the practice session. For example, the software program can prompt the coach to: provide Sunscreen to a particular player; move the particular player to a shaded area of a field; shift the particular player to indoor training exercises; bench the particular player; or send the particular player to a training facility during or after the practice session for recovery assistance; etc. if the particular player's total Sun exposure, predicted future Sun exposure, or ultraviolet exposure rate exceeds assigned levels. The software program can prompt the coach to similarly handle groups of players on the team exhibiting similar total Sun exposures, predicted future Sun exposures, or ultraviolet exposure rates.

The software program can additionally or alternatively notify training staff of Sun over-exposure of a player on the team in order to guide the training staff in assisting the particular's player recovery following the practice session. Similarly, for a particular player who has been exposed to too much Sun or has been exposed to Sun at more than a prescribed threshold rate during a previous practice session, the software program can prompt the coach (or assistant, etc.) to assign an indoor activity (e.g., weight lifting) or a lower-intensity activity (e.g., skills training) to the particular player or to bench the particular player during a next practice session in order to allow the player to fully recover from this over-exposure.

The software program can implement similar methods and techniques during a competition, such as to guide the coach in predicting performance of players later in the competition and to guide the coach in substituting players to compensate for sun (over)exposure. The software program can also store these ultraviolet exposure and ultraviolet exposure rate data in a database, such as paired with a measured or forecast UV index at the time and location of the practice session or competition.

4.4 Cooperation of Multiple Sensors

Additionally or alternatively, the exposure-tracking module 110 can cooperate with other exposure-tracking modules worn at other locations of the athlete's body, worn by other athletes within an athletic team, arranged on or near a practice field during a training session, etc. For example, a first athlete of an athletic team may wear a first exposure-tracking module 110 integrated into a watch or wristband; a second athlete on the athletic team may wear a second exposure-tracking module 110 coupled to a jersey; and a third athlete on the athletic team may not wear an exposure-tracking module 110. Furthermore, a trainer for the athletic team may arrange a third exposure-tracking module 110 on or near a practice field such that when the athletic team practices on the practice field, the third exposure-tracking module 110 near the practice field can detect and estimate solar radiation exposure for all athletes on the practice field. In this example, the first, the second, and the third exposure-tracking modules can cooperate to estimate solar radiation exposure levels for the third athlete and other athletes of the athletic team who may not wear an exposure-tracking module 110 during a practice session. Furthermore, in this example, the first, the second, and the third exposure-tracking modules can cooperate to identify and correct outlier solar irradiance values in order to improve accuracy of solar radiation exposure data by increasing the quantity of solar radiation exposure data streams.

4.5 Practice Planning

In another implementation, the software program: accesses a forecast UV index and/or solar radiation level during a time and at a location of an upcoming practice session; predicts an ultraviolet exposure of players on the team during the upcoming practice session based on this forecast UV index, historical player ultraviolet exposure data, and historical UV index data; and serves guidance to the coach (or assistant, trainer, etc.) in adjusting a training schedule for the team based on the ultraviolet exposure predictions. For example, the software program can: predict a delay to the start of the next practice session that will reduce Sun over-exposure to less than a threshold proportion (e.g., 15%) of the team; and serve a prompt to the coach to delay the next practice session to later in the same day— when the forecast UV index is lower—accordingly.

In another example, the software program can predict Sun over-exposure in at least a threshold proportion (e.g., 25%) of the team during an afternoon practice session based on a forecast UV index and solar irradiance at the time and location of the afternoon practice session; and then prompt the coach to shift a conditioning-centric workout from the upcoming afternoon practice session to a proactive session scheduled for the next morning (i.e., when the forecast UV index is lower) and to shift a skills-centric workout from the next morning practice session to the upcoming afternoon practice session if slicing mechanism predicts that more than a threshold proportion of the team (e.g., 15%) will experience Sun over-exposure during the next afternoon session based on the forecast UV index for the same time and location. In another example, the software program can estimate a duration of the next scheduled practice session that limits predicted Sun over-exposure to less than a threshold proportion (e.g., 15%) of the team and prompt the coach to limit the length of the next scheduled practice to this duration. The software program can thus prompt the coach to adjust, delay, or reschedule conditioning-centric outdoor workouts to times and/or days for which lower UV indices are forecast, thereby enabling the coach to push players to their true exhaustion rather than to a premature exhaustion predicated on over-exposure to Sunlight (e.g., excess skin temperature resulting from excess Sun exposure) such that the players' true endurances improve as a result of these conditioning-centric practice sessions.

For example, the system 100 can transmit a prompt to the user portal to render a change in training times for a particular athlete, such as recommending that the particular athlete train outdoors from 10 am-12 pm instead of 8 am-10 am over the following four days. Based on the change in training times, the system 100 can also estimate solar radiation exposure from 10 am-12 pm over the following four days (e.g., from weather information and past solar radiation exposure models) to anticipate a solar radiation exposure.

The software program can additionally or alternatively estimate a difference in predicted performance of all or select athletes on the team given a current practice schedule and a suggested practice schedule or adjustment (e.g., a "25% to 35% reduction in endurance during the upcoming training session") and provide these data to the coach in order to assist the coach in deciding whether to adjust the current practice schedule.

Additionally or alternatively, the system 100 can transmit a command to a computing device, such as a smartphone, to render within a user portal a prompt, alert, message, or other notification. As described below, the system 100 can tailor the prompt to the stake-holder accessing a user portal rendered by the computing device.

In one implementation, the system 100 can transmit the command to render, within the user portal accessed by a coach of an athletic team including athletes wearing the exposure-tracking module 110, prompts pertaining to how the coach may adjust the training for the athlete to avoid injury and over-exposure to solar radiation (UV, visible and/or IR). In this implementation, the user portal can render a list of every athlete on the athletic team's roster, each athlete's current solar radiation exposure, and classification of each athlete's current solar radiation exposure.

Furthermore, the user portal can identify (e.g., highlight or render near a top of the user portal) athletes with excessive (or high) ultraviolet exposures, for example. The user portal can then render an alert recommending the coach remove athletes with excessive ultraviolet exposures from play, activities that increase injury risk, and suspend strenuous training activities for a window of time until the athlete is able to recover from overexposure to solar radiation. Likewise, the user portal can render a list of activities appropriate for an athlete based on the athlete's current solar radiation exposure. For example, for a first athlete with current solar radiation exposure exceeding a sufficient level, the user portal can render a list of activities including: tackle football, springboard gymnastics, anaerobic training (or "sprinting"), weight-lifting, and aerobic running.

In response to detecting the current ultraviolet exposure remaining below the threshold ultraviolet exposure, the system 100 can transmit a command to render a prompt in the user portal to suspend strenuous athletic activity, such as weight-lifting, anaerobic exercise, high impact training, and long-duration aerobic exercise for a period of diminished activity. Furthermore, the user portal can render a list of activities for the athlete to perform during the period of diminished activity to decrease ultraviolet exposure and, therefore, decrease the athlete's risk of Sun damage.

In another implementation, the system 100 can transmit the command to render, within the user portal accessed by an athletic trainer or physician of a team of athletes wearing the exposure-tracking module 110, prompts indicating each athlete's current ultraviolet exposure, classification of the current ultraviolet exposure, and, based on the classification of the current ultraviolet exposure, a plan to maintain or decrease ultraviolet exposures. Generally, in this implementation, the user portal can render prompts relating to each athlete within an athletic team and targeted toward an athletic trainer with an interest in maintaining each athlete's well-being and performance capacity. Thus, the user portal can render suggestions for training modifications for each athlete recommended to decrease ultraviolet exposure.

In particular, the user portal can render a list of athletes ordered according to descending ultraviolet exposures over a period of time, such as hours, or days, or weeks or months. Thus, the user portal can highlight athletes with high risk for injury due to low ultraviolet exposures so that the trainer and/or physician can devote more time to helping athletes with high risk for injury from training sessions and avoid disadvantageous training exercises. For example, the user portal can render a list of athletes likely to need an ice bath after practice to cool their muscles from overheating due to excessive ultraviolet exposure However, the system 100 can transmit any other prompts, alerts, goals, data, or messages to the user portal in any other suitable way.

However, the software program can provide any other guidance to the coach, coach's assistant, or trainer, etc. affiliated with the team in order to reduce, limit, or control ultraviolet exposure in players on the team based on garment-related data, incident solar radiation data collected from garments worn by team members, and/or forecast UV indices and solar radiation for any other sport or team.

The systems and methods described herein can be embodied and/or implemented at least in part as a machine configured to receive a computer-readable medium storing computer-readable instructions. The instructions can be executed by computer-executable components integrated with the application, applet, host, server, network, website, communication service, communication interface, hardware/firmware/software elements of a user computer or mobile device, wristband, smartphone, or any suitable combination thereof. Other systems and methods of the embodiment can be embodied and/or implemented at least in part as a machine configured to receive a computer-readable medium storing computer-readable instructions. The instructions can be executed by computer-executable components integrated by computer-executable components integrated with apparatuses and networks of the type described above. The computer-readable medium can be stored on any suitable computer readable media such as RAMs, ROMs, flash memory, EEPROMs, optical devices (CD or DVD), hard drives, floppy drives, or any suitable device. The computer-executable component can be a processor but any suitable dedicated hardware device can (alternatively or additionally) execute the instructions.

As a person skilled in the art will recognize from the previous detailed description and from the figures and claims, modifications and changes can be made to the embodiments of the invention without departing from the scope of this invention as defined in the following claims.

The invention claimed is:

1. A system for tracking and responding to Sun exposure comprising:
    a housing configured to transiently attach to a port on a first garment;
    a jack coupled to the housing configured to transiently engage a port on the first garment;
    a radiation sensor arranged in the housing and configured to detect solar radiation incident on the housing; and
    a controller configured to:
        read an identifier of the first garment from the port via the jack;
        based on the identifier, estimate a skin exposure of a user wearing the first garment;
        read a solar radiation value from the radiation sensor at a first time; and
        based on the solar radiation value and the skin exposure, estimate a solar radiation exposure of the user at the first time.

2. The system of claim 1, further comprising:
    a wireless communication module arranged in the housing and configured to broadcast the solar radiation exposure to a mobile computing device; and
    a native application configured to execute on the mobile computing device and to render the solar radiation exposure.

3. The system of claim 2, wherein the controller is configured to serve a prompt to the native application in response to the solar radiation exposure exceeding a threshold solar radiation exposure, the user exhibiting skin damage in response to the solar radiation exposure exceeding the threshold solar radiation exposure.

4. The system of claim 1:
    wherein the housing is configured to transiently attached to a second garment;
    wherein the jack is configured to transiently engage a second port on the second garment; and
    wherein the controller is configured to read a second identifier of the second garment from the second port via the jack.

5. The system of claim 1:
    further comprising an orientation sensor arranged within the housing and configured to detect an orientation of the housing; and
    wherein the controller is configured to:
        read the orientation of the housing; and
        estimate a geospatial location and orientation of the radiation sensor based on the orientation of the housing and the identifier of the first garment.

6. The system of claim 1, wherein the controller is configured to:
    access a solar rejection ratio value of the first garment representing rejection of solar radiation through the first garment to the user's skin; and
    adjust the solar radiation exposure based on the solar rejection ratio of the first garment.

7. The system of claim 1, wherein the controller is configured to:
    based on the identifier, access a set of complementary garments worn by the user at the first time; and
    estimate the skin exposure based on an estimated proportion of the user's skin exposed to direct Sunlight and uncovered by the first garment and the set of complementary garments.

8. The system of claim 1, wherein the controller is configured to:
estimate an erythemal dose incident at the user's skin at the first time;
calculate a cumulative erythemal dose for the user over a time window based on the erythemal dose and prior erythemal doses recorded over the time window preceding the first time; and
in response to the cumulative erythemal dose exceeding a threshold erythemal dose, serving a prompt to the user to avoid additional solar radiation exposure.

9. A method for tracking and responding to Sun exposure comprising:
reading an identifier of a first garment worn by a user;
estimating the skin exposure of a user wearing the first garment based on the identifier;
at a first time, reading a solar radiation value from a radiation sensor transiently coupled to the first garment; and
based on the solar radiation value and the skin exposure, estimating a solar radiation exposure of the user at the first time.

10. The method of claim 9, further comprising:
calculating an erythemal dose incident on the user's skin at the first time based on the solar radiation value;
calculating a cumulative erythemal dose for the user over a time window preceding the first time by integrating the erythemal dose and prior erythemal doses, recorded during the time window, over the time window.

11. A method of claim 9, further comprising:
based on the identifier, extracting a type of activity performed by the user at the first time;
estimating a posture of the user at the first time based on the type of activity;
based on the posture and a known location of the radiation sensor on the first garment, estimating an orientation of the radiation sensor at the first time; and
adjusting the solar radiation exposure based on the orientation of the radiation sensor relative to a known position of the Sun at the first time.

12. The method of claim 9:
further comprising:
based on the identifier, extracting a type of activity performed by the user at the first time;
estimating a posture of the user at the first time based on the type of activity;
based on the posture and a known location of the radiation sensor on the first garment, estimating an orientation of the radiation sensor at the first time;
calculating a target orientation of the radiation sensor based on a geospatial location of the first garment at the first time and a solar position model;
wherein reading the solar radiation value comprises, in response to detecting alignment between the radiation sensor and the target orientation, reading the solar radiation value.

13. The method of claim 9:
further comprising predicting a set of complementary garments worn by the user in addition to the first garment at the first time based on the identifier of the first garment;
wherein estimating the skin exposure comprises estimating the skin exposure as a proportion of the user's skin exposed to direct Sunlight and uncovered by the first garment and the set of complementary garments at the first time.

14. The method of claim 9:
further comprising accessing a solar rejection ratio of the first garment representing rejection of solar radiation through the first garment to the user's skin; and
wherein estimating the solar radiation exposure comprises:
calculating a direct solar radiation exposure based on the skin exposure and the solar radiation value;
calculating an indirect solar radiation exposure based on a proportion of the user's skin covered by the first garment, the solar rejection ratio of the first garment and the solar radiation value; and
combining the direct and indirect solar radiation value to define the solar radiation exposure.

15. The method of claim 9, further comprising serving a prompt to a mobile computing device affiliated with the user to reduce exposure to Sunlight in response to the solar radiation exposure exceeding a threshold exposure.

16. The method of claim 9:
wherein reading the identifier of the first garment comprises, at a port arranged on the first garment worn by a first athlete of a team, accessing a type of garment worn by the first athlete based on the identifier of the first garment;
further comprising:
predicting a type of a second garment worn by a second athlete of the team based on the type of the first garment worn by the first athlete of the team; and
estimating a second solar radiation exposure of the second athlete at the first time based on the type of the second garment and the solar radiation exposure of the first athlete at the first time.

17. The method of claim 16, further comprising serving a prompt to a computing device affiliated with a coach of the first athlete and the second athlete to reduce Sun exposure in response to the solar radiation exposure on the athlete's skin exceeding a threshold solar radiation exposure.

18. The method of claim 17:
further comprising:
accessing historical solar radiation exposure data over a time window preceding the first time;
calculating a cumulative solar radiation exposure over the time window by integrating the historical solar radiation exposure data over the time window;
wherein serving the prompt to a computing device affiliated with the coach comprises serving the prompt to reduce Sun exposure in response to the cumulative solar radiation exposure exceeding the threshold solar radiation exposure.

19. The method of claim 9, further comprising:
accessing a current time and date;
accessing a geospatial location of the user at the current time;
based on the identifier, predicting a type of activity performed by the user at the current time;
based on the geospatial location, the type of activity, the current date and time, and historical activity data for the type of activity, accessing a route of the user over a time window succeeding the current time;
predicting solar positions at discrete locations on the route based on a solar position model;
estimating solar radiation incident on the user at discrete locations along the route;
predicting cumulative solar radiation exposure to the user over the time window on the route;

serving the cumulative solar radiation exposure predicted for the route to a mobile computing device affiliated with the user; and in response to the cumulative solar radiation exposure predicted for the route exceeding a threshold solar radiation exposure, prompting the user to select an alternative route.

20. The method of claim 19:

further comprising:

accessing a set of historical routes previously executed by the user;

predicting a solar position at the first time at discrete locations on each route in the set of historical routes based on the Solar position model defining an solar radiation model representing solar radiation values at discrete locations along each route in the set of historical routes;

predicting a cumulative solar radiation exposure to the user over the time window on each route in the set of historical routes;

selecting a particular route in the set of historical routes with a cumulative solar radiation exposure less than the threshold solar radiation exposure; and wherein prompting the user to select an alternative route comprises serving the particular route to the user.

* * * * *